US006913382B2

(12) United States Patent
Ledoux (10) Patent No.: US 6,913,382 B2
(45) Date of Patent: Jul. 5, 2005

(54) TREATMENT OF FLUIDS (76) Inventor: Denis-Michel Ledoux, 62 Fontenay, Lorraine, Quebec (CA), J6Z 1R7

( * ) Notice: Subject to any disclaimer, the term of this patent is extended or adjusted under 35 U.S.C. 154(b) by 301 days.

(21) Appl. No.: 10/258,756

(22) PCT Filed: Apr. 27, 2001

(86) PCT No.: PCT/IB01/00701

§ 371 (c)(1),
(2), (4) Date: Oct. 25, 2002

(87) PCT Pub. No.: WO01/81246

PCT Pub. Date: Nov. 1, 2001

(65) Prior Publication Data

US 2003/0133354 A1 Jul. 17, 2003

Related U.S. Application Data (60) Provisional application No. 60/200,135, filed on Apr. 27, 2000.

(30) Foreign Application Priority Data

Sep. 18, 2000 (CA) .............................................. 2320014

(51) Int. Cl.⁷ .............................. B01F 3/04; B01F 13/00
(52) U.S. Cl. ...................... 366/174.1; 366/339; 426/67; 426/235; 426/312; 426/317; 426/320; 426/590; 426/599
(58) Field of Search ......................... 426/67, 235, 312, 426/317, 320, 590, 599; 366/174.1, 339; 239/3; 261/76; 99/323.1

(56) References Cited

U.S. PATENT DOCUMENTS

| 4,175,871 A | * | 11/1979 | Suh et al. ...................... 366/79 |
| 4,508,265 A | * | 4/1985 | Jido ............................... 239/3 |
| 5,762,775 A | * | 6/1998 | DePaoli et al. ............. 204/554 |
| 5,769,155 A | * | 6/1998 | Ohadi et al. ............. 165/109.1 |
| 5,814,222 A | * | 9/1998 | Zelenak et al. ............. 210/615 |
| 6,265,025 B1 | * | 7/2001 | DePaoli et al. .......... 427/213.3 |
| 6,284,293 B1 | * | 9/2001 | Crandall et al. .............. 426/67 |
| 6,451,208 B1 | * | 9/2002 | Ledoux ...................... 210/222 |
| 2001/0050881 A1 | * | 12/2001 | Depaoli et al. .......... 366/167.1 |
| 2003/0086333 A1 | * | 5/2003 | Tsouris et al. ........... 366/173.1 |

FOREIGN PATENT DOCUMENTS

WO  WO 99/50186  * 10/1999

* cited by examiner

Primary Examiner—David Sorkin
(74) Attorney, Agent, or Firm—Eric Fincham (57) ABSTRACT A method for fixing a first fluid within a second fluid which includes the steps of mixing the first and second fluids together and subjecting the first and second fluids to an electric field and a high voltage corona like electric discharge. The method can be used, for example, to increase the oxygen content of water. It can also be used for the treatment of waste effluent. An apparatus for carrying out the process includes a fluid passageway defined between inner and outer elongated conduits with a preferably spirally configurated baffle means in the passageway and a plurality of electrode needles extending into the passageway.

12 Claims, 10 Drawing Sheets

TREATMENT OF FLUIDS

This application claims the benefit of Provisional Applicational No. 60/200,135 filed Apr. 27, 2000.

The present invention relates to the treatment of fluids and more particularly, relates to devices and methods for the treatment of fluids to change the properties thereof.

The treatment of a fluid with either a magnetic field or an electric field is well known in the art. For example, it is known to treat water to reduce problems associated with scaling and corrosion of the equipment using the water. In particular, the use of high temperature water in boilers and the like has caused significant problems and there have been proposals in the art for treating the water in order to reduce problems of scaling and corrosion.

It is also known in the art to use electrostatic fields to treat the water such that particles in suspension become charged and can be attracted and/or repelled as desired. This principle is also used in processes such as paint spraying and photocopiers.

While the use of electrostatic fields has been known in the art, there has been minimal acceptance of the use of such devices. Furthermore, the use of such devices has been limited to very specific situations.

Thus, German Patent 197 17 495 A1 teaches the use of an electric discharge with a plasma effect on fluids in the presence of gas generated by the corona effect.

German Patent 198 30 956 A1 teaches a method using electrical pulsation to kill biological pollutants.

U.S. Pat. No. 4,175,871 teaches a fluid mixing apparatus having means for producing vortex like motions of the fluids; the patentee teaches generation of electric fields producing an enhanced overall mixing process.

U.S. Pat. No. 5,235,905 teaches a method to create a preservation effect on perishable foods by using a pulse electrical arc in a pressurized environment.

U.S. Pat. No. 4,085,170 teaches a method for dispersing homogeneously the gas in a liquid using electrical discharge which increases a surface contact of the gas in a liquid by breaking the gas bubbles into micro bubbles.

U.S. Pat. No. 5,766,447 teaches a method of killing microorganisms in an aqueous solution using AC energy with pulsation.

WO 94/16809 teaches the use of a high voltage electrical current pulsator to purify a liquid by discharging a pulsation between two electrodes creating a plasma and forming a shock wave.

WO 99/47230 teaches a high voltage pulsation creating an acoustic shock wave and generating a plasmic reaction.

It is an object of the present invention to provide an apparatus which may be used to treat fluids with an electrostatic discharge.

It is a further object of the present invention to provide a method for the treatment of a fluid to change the characteristics of the fluid.

It is a further object of the present invention to provide a method for the fixation of a first fluid within a second fluid.

It is a further object of the present invention to provide a method for the fixation of a gas within a different fluid.

It is a further object of the present invention to provide a method for reducing the contamination of a fluid.

It is a particular object of the present invention to provide a method for a fixation of oxygen in water.

According to the present invention, in a method for fixing a first fluid in a second fluid comprising the steps of mixing the first and second fluids together, there is the improvement which comprises the step of passing the fluid between two electrodes, a first one of the electrodes being formed of a metallic material having a dielectric covering thereon, a second one of the electrodes being formed of a metallic material and being grounded, and applying a DC voltage to the first of the electrodes.

In a further aspect of the present invention, in an apparatus for fixing a first fluid in a second fluid wherein the apparatus has an outer elongated conduit, an inner coaxial conduit, the inner coaxial conduit being of a metallic material and having a dielectric material coated thereon, a fluid passageway defined intermediate the outer elongated conduit and inner coaxial conduit, means for introducing a first and second fluid into the fluid passageway, spirally arranged baffle means within the fluid passageway to cause fluids passing therethrough to circulate in a spiral configuration, a plurality of electrode needles in electrical communication with the outer conduit and extending inwardly towards the inner coaxial conduit, the improvement comprising a conical section formed between opposed ends of the inner and outer conduits, the conical section having a decreasing cross sectional area in the direction of fluid flow, and means for applying a DC voltage to the inner conduit, the baffle means being electrically grounded.

In a preferred embodiment, the baffle means are mounted within the fluids passageway to cause a fluid introduced at a first end of the passageway to circulate in a spiral configuration therein. A particularly preferred arrangement comprises one wherein a spiral member is used wherein the inwardly extending edge of the spiral member has a tapered sharp configuration. Even more preferably, there are provided a plurality of electrode needles which can cause a corona like discharge.

Preferably, the system of the present invention is designed to be operated at a voltage of at least 10 kV.

The ability of a liquid to hold soluble a gas is finite and is a function of both pressure and temperature. One everyday example of utilizing a pressure to maintain a gas soluble is that of soda drinks wherein they are carbonated and maintained under pressure to maintain the gas soluble within the liquid. Once the cap is removed and pressure is released, the solubility of the gas decreases and over time, the drink will go flat.

According to one method of the present invention, when a gas is introduced to a liquid, both being under pressurization, and the liquid and dissolved gas are passed through an electric field having a voltage of at least ±10 kV, the gas will remain "dissolved" in the liquid beyond the normal capacity of the liquid to hold such a gas. Preferably, the voltage will be ±15 kV.

The mechanism for the ability of the gas to remain within the liquid is not fully understood. Thus, while applicant will use the term "dissolve", it is well understood that a different mechanism other than the standard definition of solution may be employed. For purposes of this application, applicant will use the terms "fix" or "fixation" as a description of the mechanism of retention of the gas within the liquid.

However, applicant does not intend to be limited by this term; rather, it will be understood that any bonding mechanism or other means of retaining the gas within the liquid will fall within the scope of the invention when the method of the invention is practiced.

The method of the present invention can be applied with many different fluids. First of all, one can have a fixation of a gas within a liquid, a fixation of a first gas within another gas, or a fixation of a liquid within a second liquid. The scope of the present invention also includes the fixation of a liquid to a gas. Still further, the present invention can be practiced for the fixation of a liquid or a gas with certain types of solids, and particularly flowable solids.

The particular gas/liquid/solid will depend upon the particular end use desired. Some of the possibilities are discussed herein below.

A first method of the present invention would involve the fixation of a gas within a liquid. Many uses for such a method can be envisaged including, for example, the fixation of oxygen within water. The use of such a material can range widely from medicinal use to the treatment of cyanide containing water such as is encountered in many mining operations. Other potential uses would include, for example, a nitrogen gas within a liquid for use as a fertilizer. One suffices to say that wherever the use of a particular gas in conjunction with a liquid is desirable, the method of the present invention can be practiced within the limits dictated by normal practice—i.e. a question of the safety of the product involved including either the liquid or the gas.

A method of the present invention can also be utilized to treat food products for various purposes including the ability to enhance the storage of the products and/or the use of the invention as a bactericide. Thus, the present invention can be utilized as a cold pasteurization of products such as milk and/or juices and the like.

A further method of the present invention would involve the treatment of a flowable product such as a resin which has been used in a treatment system wherein the resin adsorbs/absorbs different chemicals on its surface. With the method of the present invention, one can pass the resin through the treatment of the present invention to renew the resin. Furthermore, one can use a gas to fixate the gas within the resin to enhance the efficacy thereof.

A unique feature of the present invention is the fact that the gas will remain "fixed" within the liquid for a substantial period of time. Referring to the case of oxygen within water, when get in a bottled condition, there is minimal loss of the properties—i.e. the oxygen remains fixed. When exposed to air ambient temperature, there is a loss, in one week, of between 5%–10% of the fixed oxygen. It is being found that freezing the water with the fixed oxygen causes a substantial loss of oxygen content. However, one can boil the water with fixed oxygen with some loss thereof. The oxygen content is preferably between 50 and 100 ppm although it can reach as much as 140 ppm.

A further aspect of the present invention comprises the treatment of a fluid to decontaminate the fluid. Examples of such fluids can range from waste products from industrial processes through to municipal sewage. It has been found that treatment of the waste material is highly effective in removing contaminates and in purifying the liquid.

Having thus generally described the invention, reference will be made to the accompanying drawings and examples showing embodiments thereof, in which.

Initially, it will be understood that the specific descriptions herein relating to the treatment of water or a liquid with a gas may equally well be applied to other materials as discussed hereinabove.

Figure 1:
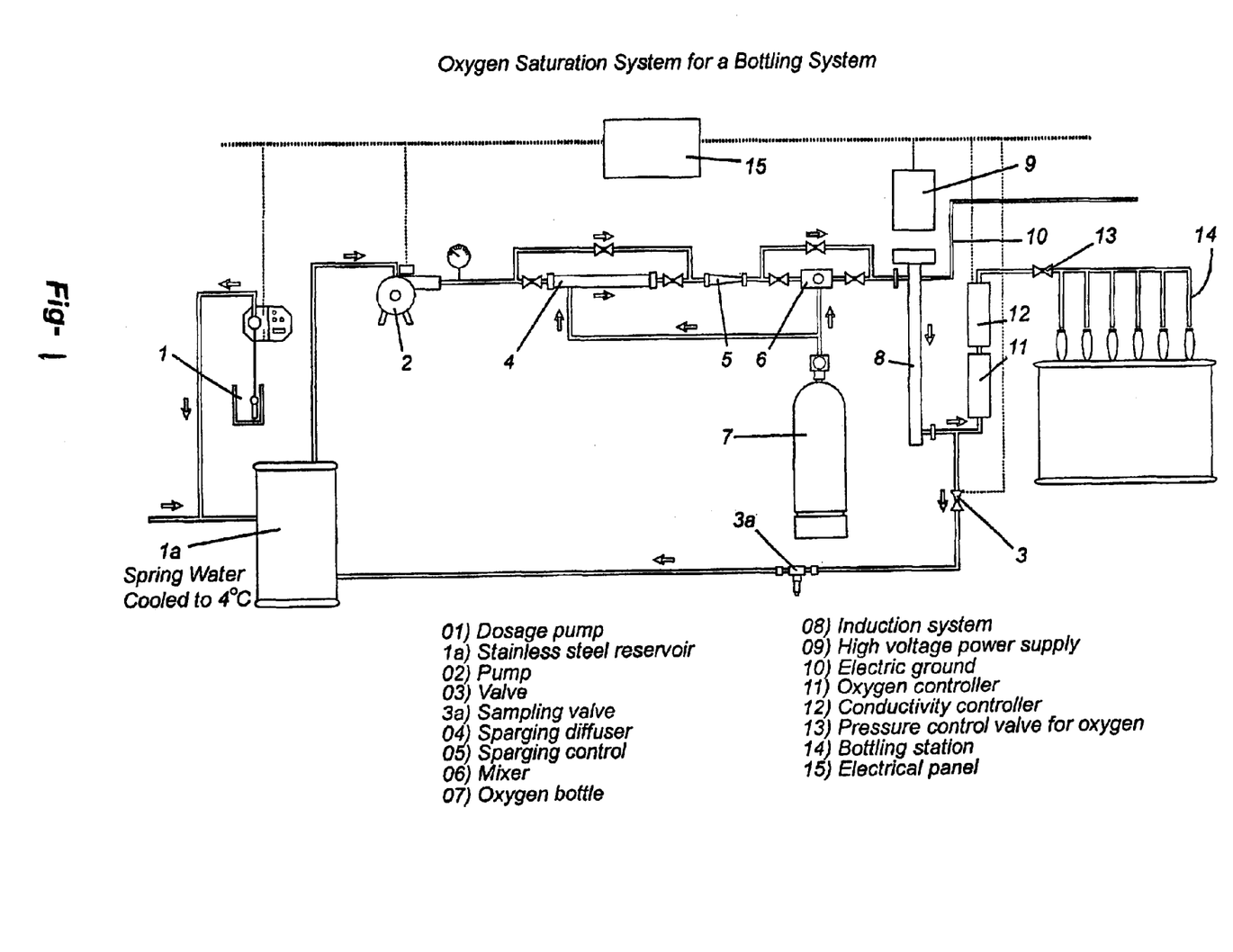
FIG. 1 is a schematic illustration of a first system for the treatment of water with a gas such as oxygen for the bottling thereof.

Turning to FIG. 1, there is shown a system for providing oxygen rich water which may be bottled. In this arrangement, there is provided a dosage pump 1 operatively associated with a reservoir 1A of water cooled to approximately 4° C. A pressure pump 2 is operatively connected to an outlet conduit which in turn leads to a membrane sparging diffuser having a control member 5 associated therewith. A mixer 6 is connected to a bottle of oxygen 7 and the gas and water will then pass through the induction system 8 of the present invention. Induction system 8 is provided with a high voltage power supply 9 and a special ground 10.

An oxygen controller 11 is provided as well as a conductivity controller 12. A jig or valve structure 13 is provided for controlling and maintaining the pressure of the oxygen within the water. Subsequently, the water will go through a bottling station 14. A control panel 15 provides suitable controls for the operation of the system.

Figure 2:
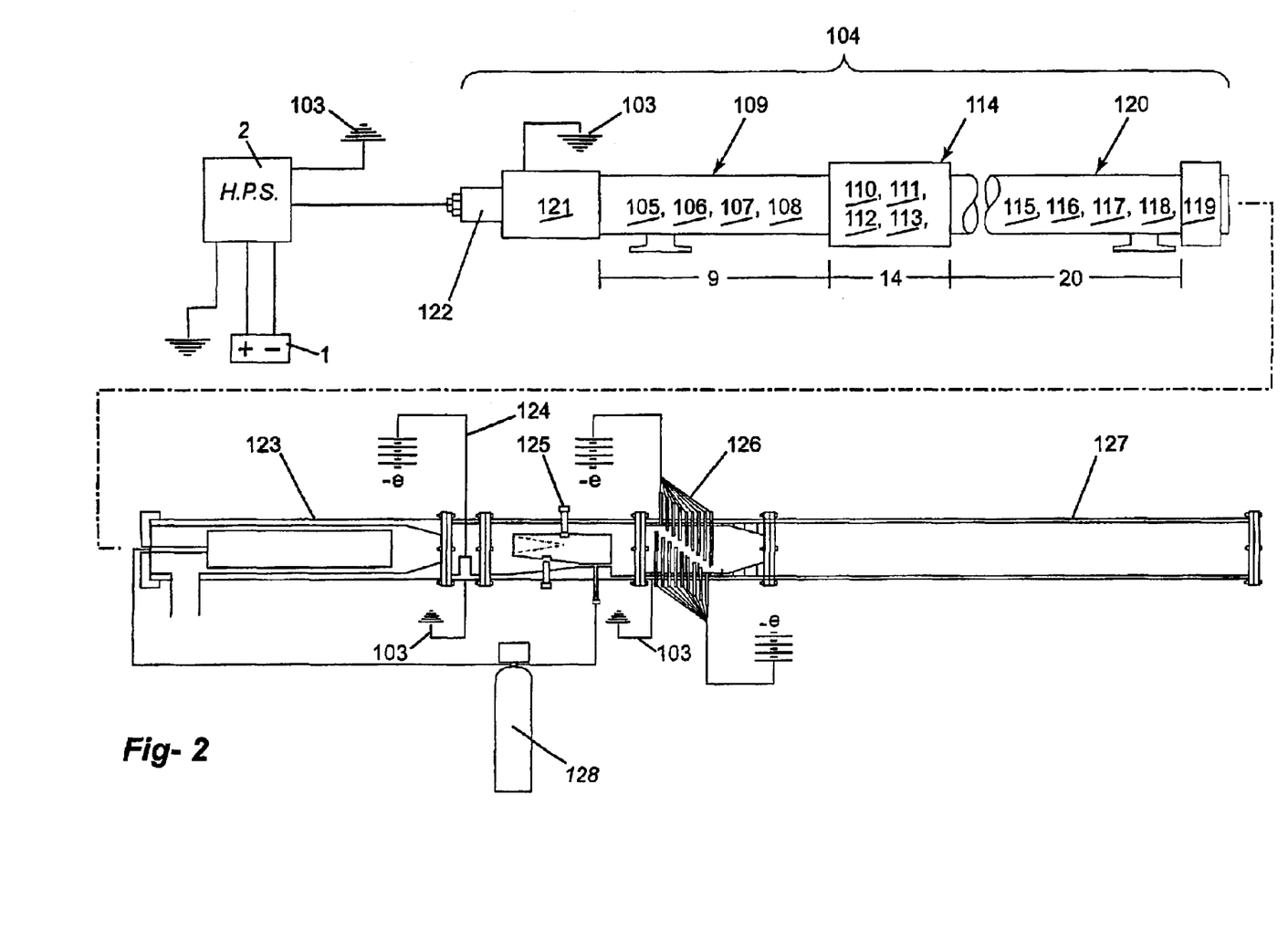
FIG. 2 is a schematic illustration of a system for the fixation of a gas within a liquid.

Turning to FIG. 2, there is illustrated a second system for the fixation of a gas such as oxygen in a liquid such as water. In this arrangement, there is provided a suitable electric source 101 connected to a high power supply 102 capable of supplying electricity at a voltage of 50 kV DC or above. A suitable ground 103 is provided.

There is provided an induction device generally designated by reference numeral 104 and which includes, within the device, a conductor 105, a dielectric 106 in a Teflon material, a spiral 107 of a metallic material such as stainless steel, and an outer envelope 108. This is all encompassed in a first section 109 of the induction system. This is substantially as shown in PCT/CA/99/00274, the disclosure of which is hereby incorporated.

In a second section 114, there is provided a conductor 110 in a conical arrangement, a spirally wound dielectric 111 in a conic configuration and a spiral 112 in stainless steel. This is all contained in an outer package 114.

In a third section 120, there is again provided a conductor 115, a spirally wound dielectric 116, stainless 117 and an outer envelope or container 118. This is all contained in a package 120.

The arrangement includes a entry 122 for the conductor wires and a diffuser membrane 123. Reference numeral 124 indicates an ionization by a dielectric effect. There is provided a diffuser 125 to permit the entry of a gas into the water while there is provided a multiple point ionization arrangement 126 which provides a corona effect by a cycling system preferably at 50 kV or above and with a current of 5 MA or above.

Subsequently, there is provided a mixer 127.

Figure 3:
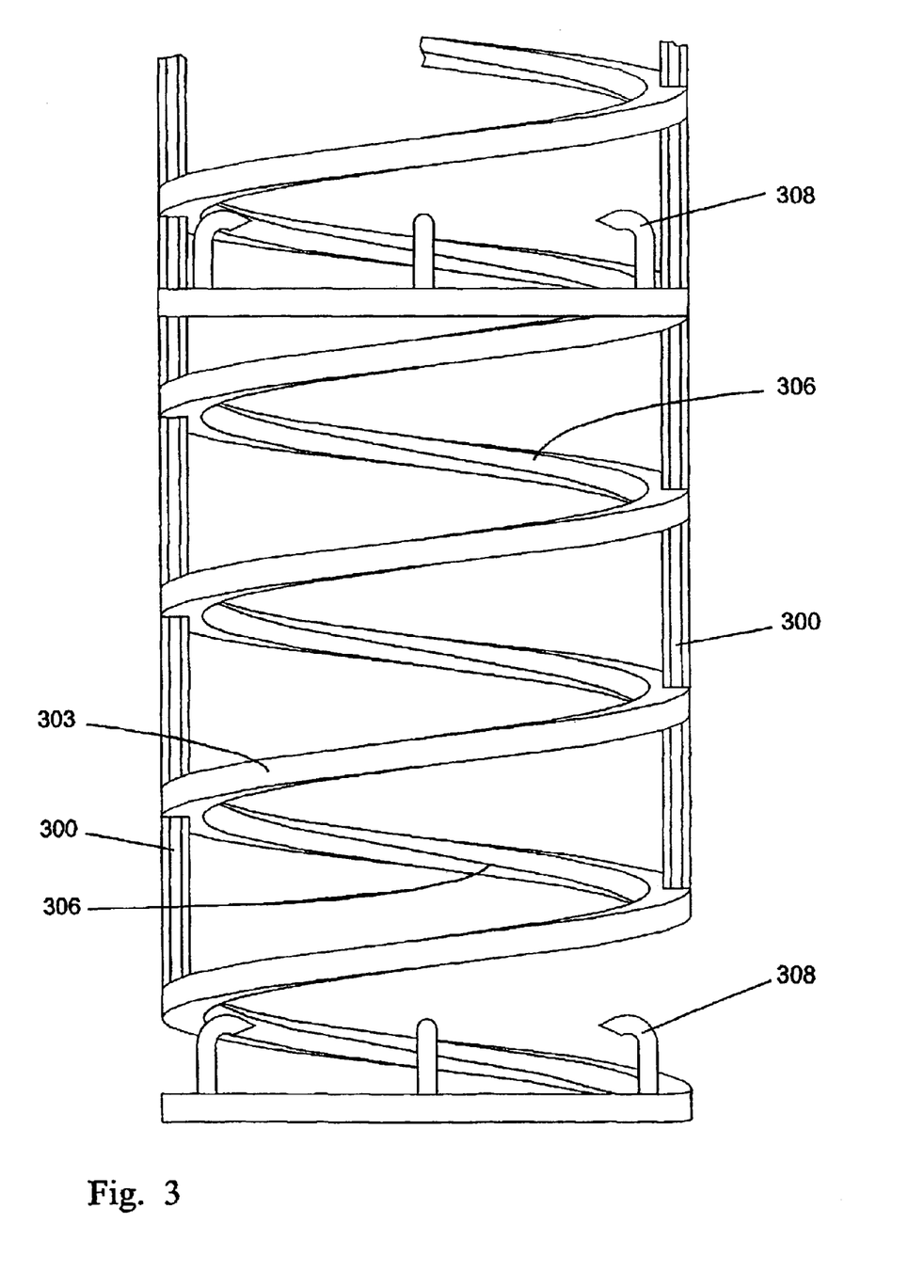
FIG. 3 is a side elevational view of a spiral component for use in causing an electrical discharge within the water.
Figure 4:
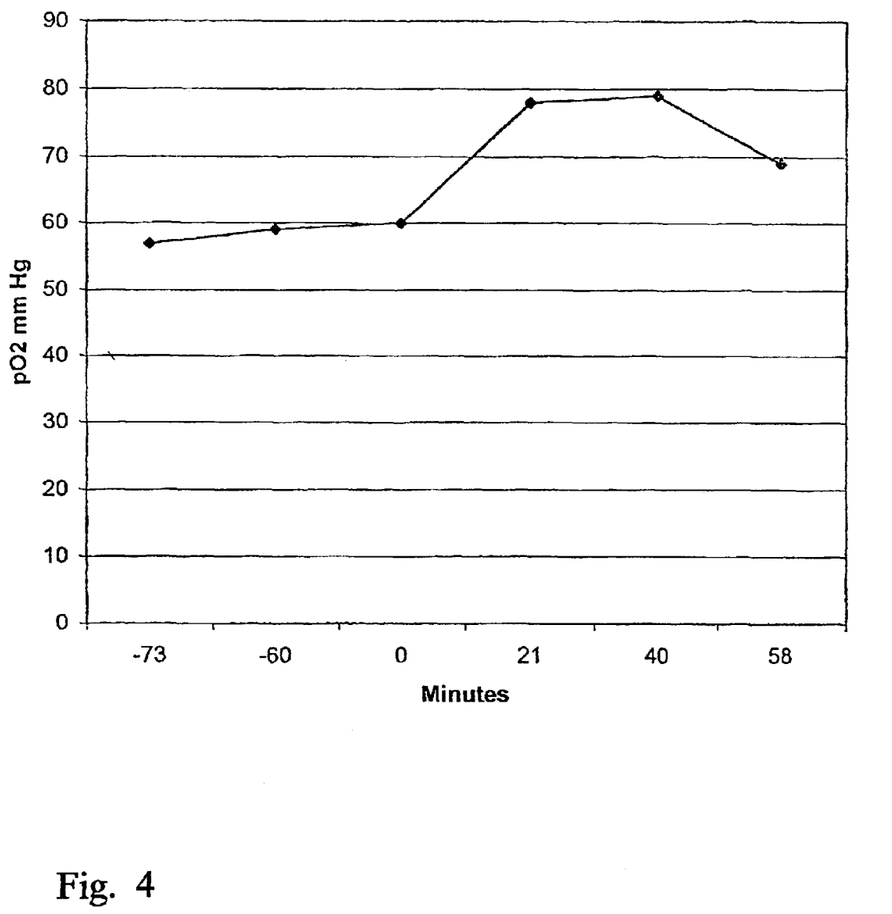
FIGS. 4 to 10 are graphs illustrating the measurement of blood oxygen after intake of oxygenated water as set forth in Example 10.
Figure 5:
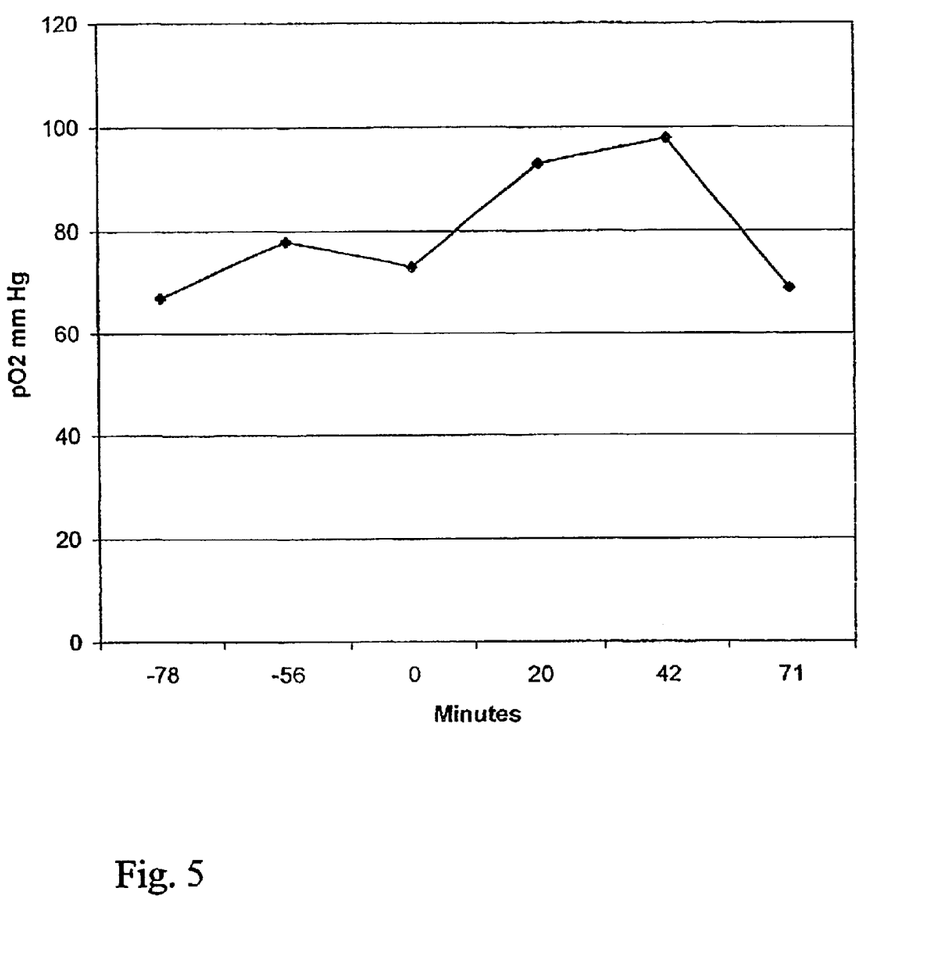
Figure 6:
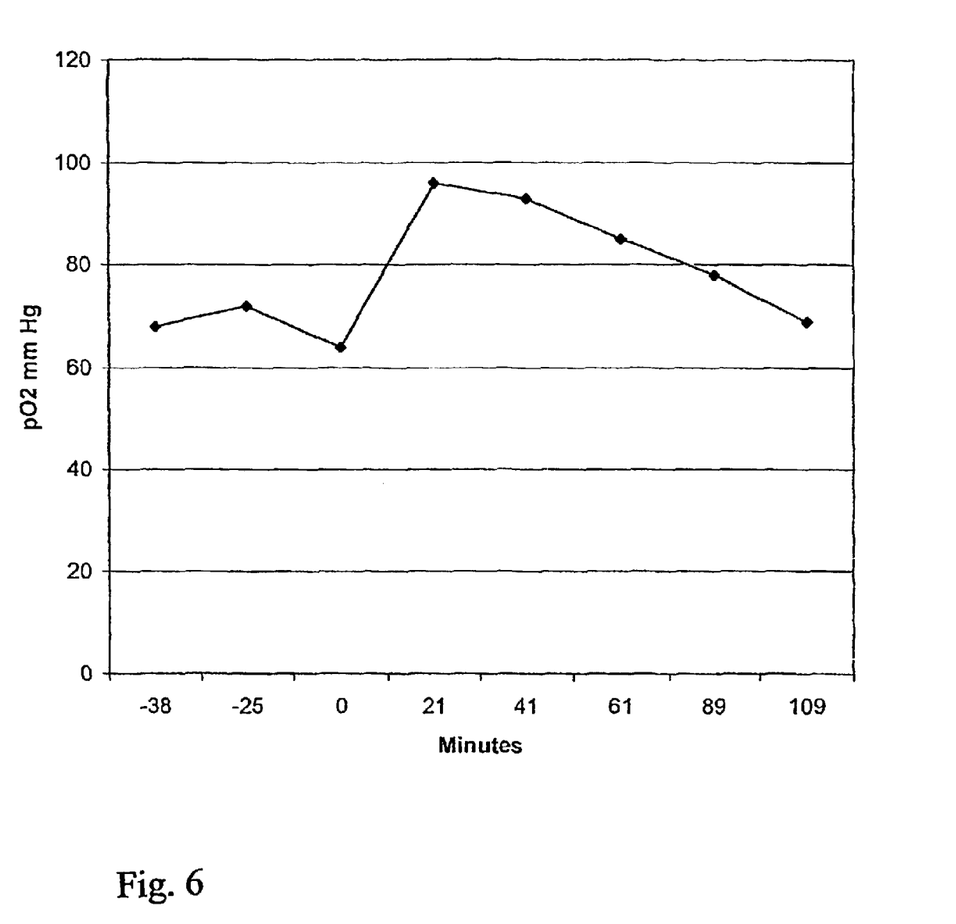
Figure 7:
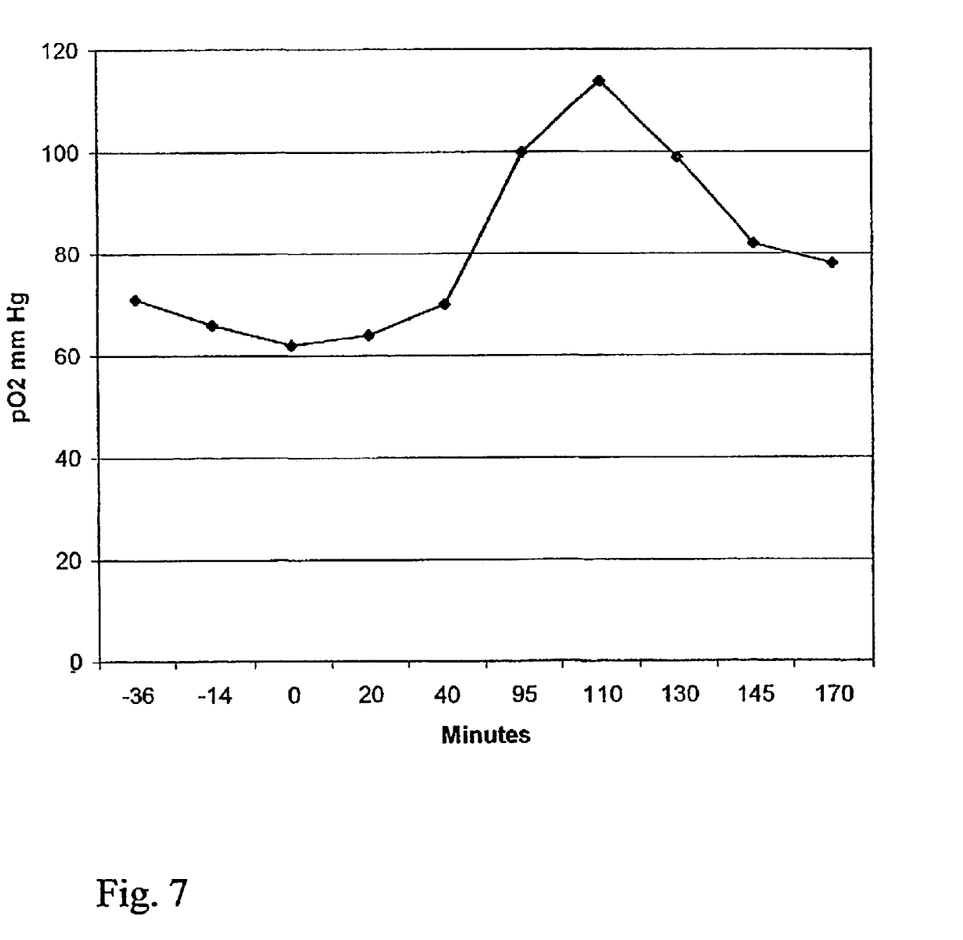
Figure 8:
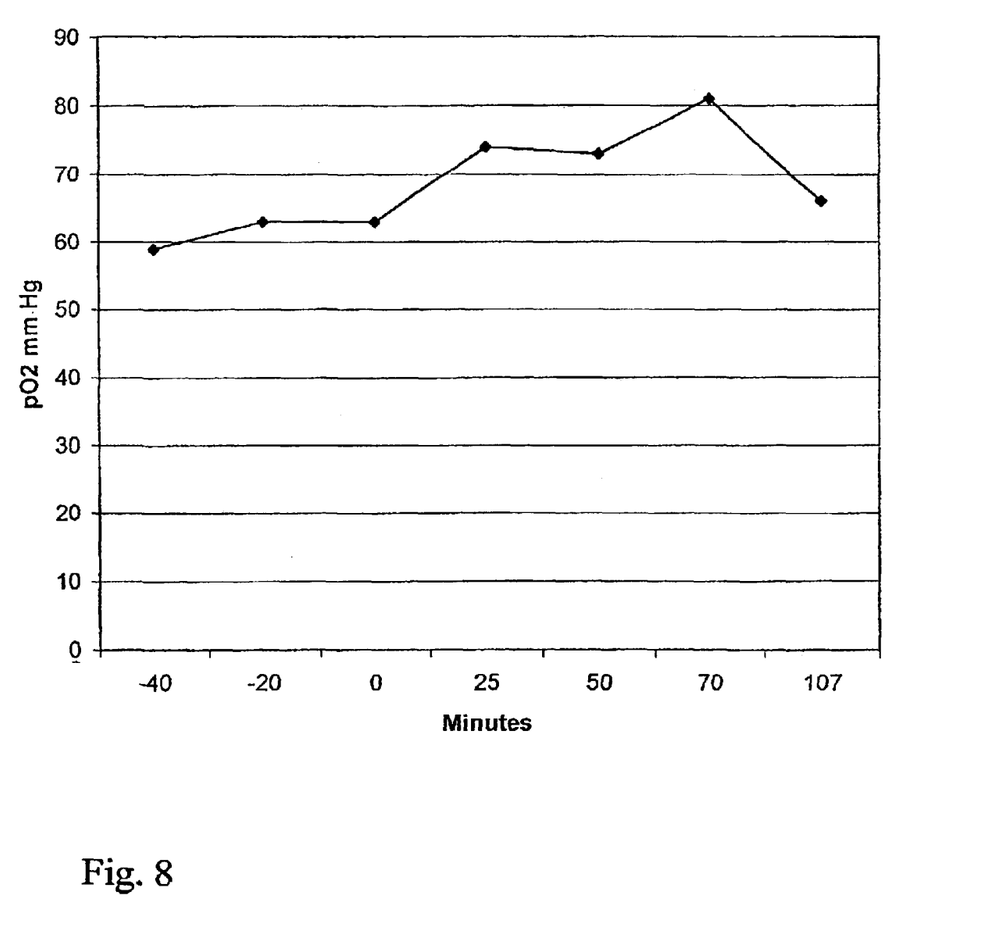
Figure 9:
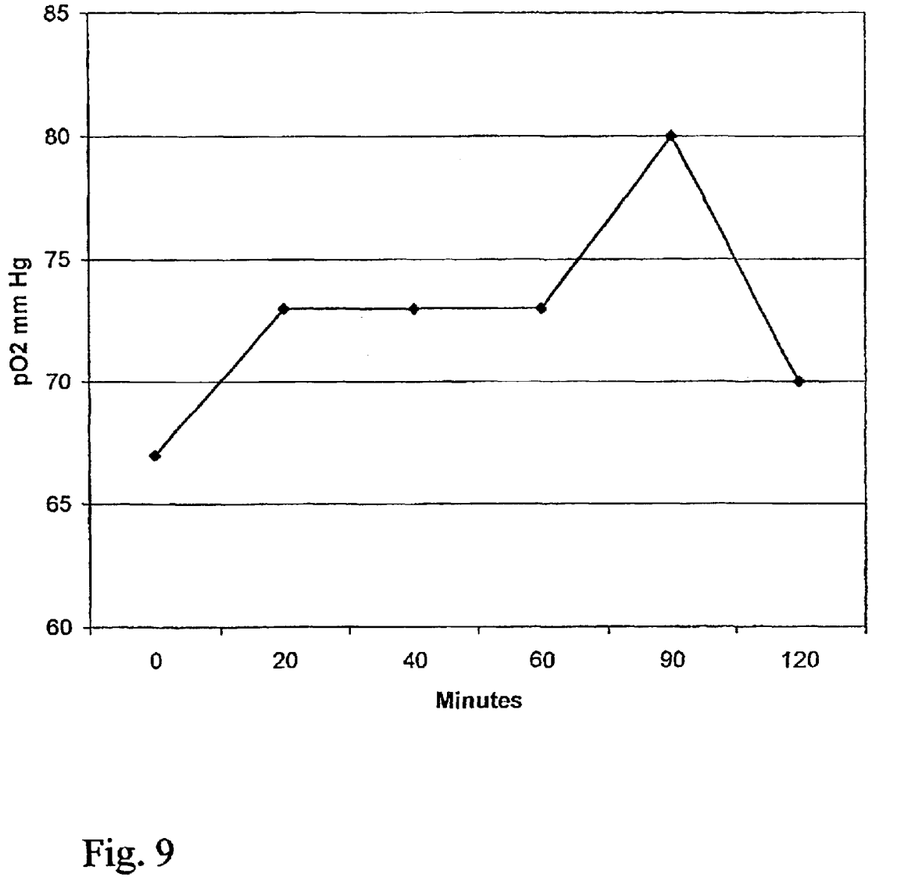
Figure 10:
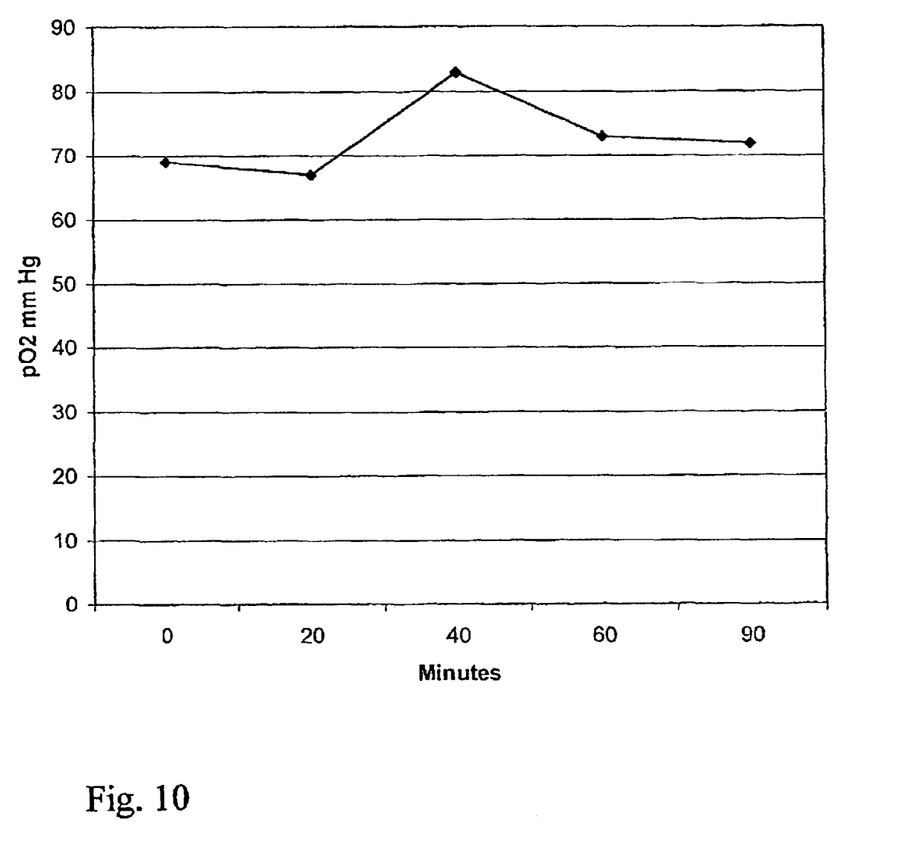

As shown in FIG. 3, interiorly there is provided a member within the conduit for electrical discharge. As shown, there are a pair of side bar members 300 with a spirally wound member 303 having tapered edges extending inwardly to provide a sharp point generally designated by reference numeral 306.

At points along the spiral, there are provided discharge electrodes 308 which again are provided with a sharp point and are designed to discharge at intervals to provide a corona effect.

The following examples are illustrative of some of the different aspects of the present invention.

EXAMPLE 1

Municipal waste from an urban municipality were subjected to a treatment in an apparatus according to the present invention. The waste water was treated without using any gas, using air, oxygen, carbon dioxide and nitrogen. The results are given in Table 1, hereinbelow.

| Parameters | Units | Control Not Treated | Treated No gas | Air | $O_2$ | $CO_2$ | $N_2$ |
|---|---|---|---|---|---|---|---|
| pH | | 7.15 ±0.01 | 7.29 ±0.07 | 7.34 ±0.11 | 7.41 ±0.04 | 5.39 ±0.05 | 6.40 ±0.07 |
| POR | (mV) | 112 ±23 | 89 ±28 | 111 ±1 | 141 ±4 | 179 ±4 | 124 ±9 |
| T° | (° C.) | 19.8 ±0.5 | 19.8 ±0.1 | 20.5 ±0.1 | 20.6 ±0.2 | 20.9 ±0.2 | 21.1 ±0.4 |
| $DCO_{tot}$ | (mg/L) | 1670 ±120 | 1440 ±100 | 1790 ±400 | 1560 ±150 | 1460 ±190 | 1710 ±210 |
| $DCO_{sol}$ | (mg/L) | 113 ±25 | 115 ±35 | 80 ±35 | 95 ±10 | 120 ±20 | 80 ±15 |
| MES | (mg/L) | 113 ±37 | 117 ±15 | 169 ±33 | 187 ±26 | 182 ±15 | 177 ±40 |
| MVS | (mg/L) | 97 ±42 | 95 ±13 | 144 ±43 | 152 ±198 | 160 ±15 | 158 ±16 |
| $PO_4^{3-}$ | (mg/L) | 1.87 ±0.06 | 1.49 ±0.17 | 1.68 ±0.01 | 1.73 ±0.03 | 1.76 ±0.01 | 1.60 ±0.01 |
| $NH_4^+$ | (mg/L) | 15.1 ±0.6 | 12.8 ±1.6 | 14.7 ±0.1 | 14.6 ±0.3 | 14.7 ±0.8 | 14.0 ±0.5 |

Explanation:
POR—Oxygen Potential Reduction
$DCO_{tot}$—Chemical Oxygen Demand (Total)
tot—Total
$DCO_{sol}$—Chemical Oxygen Demand (Solution)
sol—Solution
MES—Material in Suspension
MVS—Material in Suspension (Volatile)

From the above results, the treatment without a gas and with the addition of carbon dioxide permitted a reduction in the concentration of DCO sub-total without affecting the DCO sub-base.

EXAMPLE 2

The solid waste from a municipal plant was subjected to treatment with the apparatus of the present invention. The trials were carried out using the injection of air, oxygen, carbon dioxide and nitrogen. A trial was also run without the injection of a gas. The results are set forth in Table 2 hereinbelow.

|  |  | Control | Treated | | | | |
| --- | --- | --- | --- | --- | --- | --- | --- |
| Parameters | Units | Not Treated | No gas | Air | $O_2$ | $CO_2$ | $N_2$ |
| pH |  | 6.43 ±0.04 | 7.17 ±0.05 | 8.45 ±0.01 | 6.64 ±0.03 | 5.53 ±0.02 | 6.69 ±0.02 |
| POR | (mV) | −124 ±9 | 436 ±4 | 499 ±15 | 59 ±13 | 67 ±7 | −83 ±20 |
| T° | (°C.) | 17.7 ±0.2 | 19.9 ±0.1 | 21.4 ±0.1 | 20.1 ±0.3 | 21.3 ±0.3 | 22.4 ±0.1 |
| $DCO_{tot}$ | (mg/L) | 14000 ±3110 | 5510 ±1040 | 5040 ±1040 | 5230 ±800 | 5340 ±720 | 5810 ±200 |
| $DCO_{sol}$ | (mg/L) | 349 ±20 | 599 ±43 | 1010 ±60 | 397 ±7 | 476 ±6 | 383 ±9 |
| MES | (mg/L) | 4860 ±30 | 4020 ±60 | 3280 ±100 | 3710 ±30 | 3570 ±50 | 3720 ±100 |
| MVS | (mg/L) | 3330 ±30 | 2690 ±40 | 2180 ±80 | 2610 ±30 | 2630 ±20 | 2670 ±70 |
| $PO_4^{3-}$ | (mg/L) | 1.59 ±0.06 | 3.55 ±0.17 | 5.77 ±0.02 | 2.66 ±0.21 | 2.27 ±0.10 | 2.92 ±0.35 |
| $NH_4^+$ | (mg/L) | 47.0 ±1.4 | 41.3 ±2.3 | 11.3 ±0.7 | 54.4 ±2.7 | 52.2 ±2.7 | 54.8 ±1.8 |

March variations were noted in the POR both without injection of a gas and with injections of air. A substantial decrease in the DCO sub-total was measured with all treatments. This was accompanied by an increase in the DCO sub-base. The treatment with oxygen was interesting since it permitted a decrease of 62.6% of the DCO total while causing only a slight increase in the DCO base.

Interesting was the ability of the treatment to remove disagreeable odors. In particular, the treatment without a gas and with air substantially reduced the disagreeable odors while the remaining treatments also reduce the odors, but to a lesser degree.

EXAMPLE 3

Used water from a pulp was subjected to a treatment as set forth in Examples 1 and 2. The results are set forth in Table 3 hereinbelow.

| Parameters | Units | Control Not Treated | Treated | | | | |
| --- | --- | --- | --- | --- | --- | --- | --- |
|  |  |  | No gas | Air | $O_2$ | $CO_2$ | $N_2$ |
| pH |  | 8.67 ±0.02 | 8.54 ±0.01 | 8.59 ±0.01 | 8.66 ±0.01 | 4.63 ±0.03 | 7.92 ±0.01 |
| POR | (mV) | 3 ±25 | 5 ±3 | 23 ±1 | 47 ±2 | 200 ±3 | 65 ±9 |
| T° | (°C.) | 23.3 ±0.2 | 24.4 ±0.1 | 25.3 ±0.1 | 24.0 ±0.1 | 24.3 ±0.1 | 25.3 ±0.1 |
| $DBO_{5(sol)}$ | (mg/L) | 380 | 490 | 470 | 450 | 500 | 470 |
| $DCO_{tot}$ | (mg/L) | 1480 ±80 | 1920 ±130 | 1520 ±100 | 3050 ±240 | 2310 ±70 | 2330 ±90 |
| $DCO_{sol}$ | (mg/L) | 1190 ±160 | 1010 ±210 | 965 ±21 | 960 ±24 | 968 ±57 | 944 ±11 |
| MES | (mg/L) | 367 ±240 | 422 ±126 | 719 ±457 | 1181 ±308 | 485 ±175 | 752 ±316 |
| MVS | (mg/L) | 354 ±207 | 410 ±126 | 706 ±454 | 1160 ±270 | 461 ±201 | 717 ±304 |
| $PO_4^{3-}$ | (mg/L) | 0.61 ±0.06 | 0.55 ±0.03 | 0.54 ±0.01 | 0.53 ±0.01 | 0.57 ±0.02 | 0.47 ±0.02 |
| $NH_4^+$ | (mg/L) | 0.23 ±0.02 | 0.14 ±0.11 | 0.01 ±0.01 | 0.01 ±0.01 | 0.02 ±0.02 | 0.00 ±0.00 |

EXAMPLE 4

Solid waste from a pulp plant were subjected to a treatment with the apparatus of the present invention. The results are set forth in Table 4 hereinbelow.

|  |  | Control | \multicolumn{5}{c}{Treated} | | | | |
| --- | --- | --- | --- | --- | --- | --- | --- |
| Parameters | Units | Not Treated | No gas | Air | $O_2$ | $CO_2$ | $N_2$ |
| pH |  | 5.83 | 5.95 | 6.04 | 5.97 | 4.79 | 5.89 |
|  |  | ±0.04 | ±0.03 | ±0.03 | ±0.02 | ±0.01 | ±0.03 |
| POR | (mV) | −113 | −55 | 6 | 23 | 27 | −65 |
|  |  | ±11 | ±7 | ±12 | ±6 | ±1 | ±4 |
| T° | (° C.) | 21.9 | 25.7 | 26.6 | 27.1 | 25.6 | 24.9 |
|  |  | ±0.3 | ±0.1 | ±0.1 | ±0.2 | ±0.1 | ±0.1 |
| $DBO_{5(sol)}$ | (mg/L) | 430 | 410 | 420 | 450 | 330 | 690 |
| $DCO_{tot}$ | (mg/L) | N/A | N/A | N/A | N/A | N/A | N/A |
| $DCO_{sol}$ | (mg/L) | 624 | 947 | 1050 | 901 | 1200 | 1020 |
|  |  | ±42 | ±42 | ±20 | ±50 | ±140 | ±30 |
| MES | (mg/L) | 23500 | 17500 | 15800 | 16600 | 14700 | 17700 |
|  |  | ±400 | ±1500 | ±200 | ±600 | ±600 | ±2000 |
| MVS | (mg/L) | 22500 | 16800 | 15100 | 15900 | 14100 | 16900 |
|  |  | ±400 | ±1400 | ±200 | ±500 | ±500 | ±1900 |
| $PO_4^{3-}$ | (mg/L) | 14.3 | 14.1 | 13.8 | 13.7 | 13.8 | 15.1 |
|  |  | ±0.2 | ±0.3 | ±0.5 | ±0.2 | ±0.4 | ±0.1 |
| $NH_4^+$ | (mg/L) | 3.97 | 8.03 | 8.24 | 8.06 | 7.57 | 8.61 |
|  |  | ±0.33 | ±0.42 | ±0.65 | ±0.43 | ±1.24 | ±0.38 |

EXAMPLE 5

Liquid hog manure was subjected to a treatment with the apparatus of the present invention in the manner set forth in the previous examples. The results are set forth in Table 5 hereinbelow.

|  |  |  | \multicolumn{5}{c}{Treated} | | | | |
| --- | --- | --- | --- | --- | --- | --- | --- |
| Parameters | Units | Control Not Treated | No gas | Air | $O_2$ | $CO_2$ | $N_2$ |
| pH |  | 7.33 | 7.62 | 7.70 | 7.97 | 6.96 | 7.84 |
|  |  | ±0.02 | ±0.01 | ±0.03 | ±0.02 | ±0.01 | ±0.02 |
| POR | (mV) | −320 | −163 | −165 | −5 | −152 | −283 |
|  |  | ±6 | ±25 | ±42 | ±1 | ±36 | ±6 |
| T° | (° C) | 17.0 | 20.7 | 22.0 | 22.2 | 22.7 | 22.9 |
|  |  | ±0.3 | ±0.2 | ±0.5 | ±0.2 | ±0.2 | ±0.1 |
| $DCO_{tot}$ | (mg/L) | 36100 | 34900 | 34600 | 35300 | 32300 | 35900 |
|  |  | ±1200 | ±500 | ±1400 | ±1200 | ±1900 | ±1900 |
| $DCO_{sol}$ | (mg/L) | 9290 | 17700 | 12500 | 12600 | 14000 | 13500 |
|  |  | ±290 | ±200 | ±100 | ±700 | ±400 | ±100 |
| MES | (mg/L) | 20800 | 17200 | 18800 | 19600 | 19100 | 21900 |
|  |  | ±600 | ±500 | ±100 | ±200 | ±200 | ±100 |
| MVS | (mg/L) | 14000 | 11300 | 11300 | 12800 | 12400 | 14700 |
|  |  | ±400 | ±500 | ±100 | ±200 | ±200 | ±100 |
| $PO_4^{3-}$ | (mg/L) | 205 | 161 | 158 | 152 | 190 | 181 |
|  |  | ±6 | ±8 | ±2 | ±6 | ±18 | ±43 |
| $NH_4^+$ | (mg/L) | 3180 | 2160 | 2170 | 2250 | 2280 | 2230 |
|  |  | ±240 | ±20 | ±120 | ±30 | ±40 | ±70 |
| $P_{tot}$ | (mg/L) | 732 | 609 | 643 | 618 | 659 | 628 |
|  |  | ±33 | ±11 | ±40 | ±74 | ±52 | ±92 |
| NTK | (mg/L) | 3010 | 2540 | 3400 | 2930 | 3160 | 3710 |
|  |  | ±240 | ±80 | ±70 | ±210 | ±130 | ±620 |

The DCO sub-total was slightly diminished while the DCO total was substantially increased. The level of the phosphates and ammonium were also decreased. A decrease in the odor was also noted with a substantial decease being obtained with the use of oxygen.

EXAMPLE 6

A synthetic multi-metallic effluent was subjected to a treatment with the apparatus of the present invention. The results are set forth in Table 6 hereinbelow.

|  |  | Control | Treated | | | | |
|---|---|---|---|---|---|---|---|
| Parameters | Units | White | Not Treated | No gas | Air | $O_2$ | $CO_2$ | $N_2$ |
| pH | N/A | 2.17 ±0.02 | 2.17 ±0.01 | 2.21 ±0.05 | 2.07 ±0.02 | 2.34 ±0.02 | 2.27 ±0.01 |
| POR | (mV) | N/A | 487 ±4 | 516 ±5 | 493 ±8 | 518 ±2 | 499 ±3 | 476 ±3 |
| T° | (° C.) | N/A | 25.9 ±0.1 | 26.6 ±0.1 | 25.8 ±0.1 | 27.4 ±0.3 | 27.9 ±0.1 | 23.8 ±0.1 |
| Al | (mg/L) | 0.01 ±0.01 | 0.51 ±0.03 | 0.88 ±0.03 | 0.44 ±0.04 | 0.43 ±0.03 | 0.41 ±0.05 | 0.54 ±0.03 |
| Ca | (mg/L) | 0.19 ±0.10 | 18.3 ±0.5 | 28.2 ±0.5 | 16.5 ±0.9 | 16.1 ±1.6 | 17.6 ±1.4 | 19.1 ±0.4 |
| Cd | (mg/L) | 0.00 ±0.00 | 12.6 ±0.5 | 10.2 ±0.7 | 10.6 ±0.4 | 10.8 ±0.7 | 11.1 ±0.8 | 12.3 ±0.2 |
| Cr | (mg/L) | 0.00 ±0.00 | 1.92 ±0.10 | 1.57 ±0.12 | 1.63 ±0.06 | 1.65 ±0.11 | 1.70 ±0.12 | 1.91 ±0.04 |
| Cu | (mg/L) | 0.11 ±0.00 | 5.13 ±0.36 | 30.2 ±2.1 | 29.1 ±1.2 | 20.1 ±0.8 | 15.7 ±1.1 | 12.5 ±0.3 |
| Fe | (mg/L) | 0.20 ±0.01 | 54.1 ±29.1 | 13.6 ±0.2 | 22.1 ±0.8 | 26.7 ±1.9 | 29.9 ±2.4 | 80.8 ±1.8 |
| Mg | (mg/L) | 0.05 ±0.01 | 12.7 ±0.5 | 14.3 ±1.6 | 11.2 ±0.5 | 11.2 ±0.7 | 11.6 ±0.8 | 12.8 ±0.3 |
| Mn | (mg/L) | 0.00 ±0.00 | 3.55 ±0.23 | 2.84 ±0.23 | 2.98 ±0.13 | 3.02 ±0.18 | 3.10 ±0.23 | 3.57 ±0.07 |
| Na | (mg/L) | 0.09 ±0.05 | 53.8 ±2.5 | 57.7 ±7.7 | 45.4 ±2.1 | 46.6 ±2.9 | 48.0 ±3.5 | 53.4 ±1.3 |
| Ni | (mg/L) | 0.00 ±0.00 | 3.48 ±0.18 | 2.99 ±0.22 | 3.02 ±0.12 | 3.05 ±0.20 | 3.08 ±0.22 | 3.47 ±0.06 |
| Pb | (mg/L) | 0.02 ±0.00 | 35.0 ±1.6 | 36.9 ±2.5 | 34.9 ±1.1 | 32.7 ±1.9 | 33.5 ±2.2 | 35.4 ±0.9 |
| Zn | (mg/L) | 0.06 ±0.01 | 7.40 ±0.67 | 18.1 ±1.5 | 12.3 ±0.5 | 9.37 ±0.62 | 8.88 ±0.64 | 8.90 ±0.15 |

As will be noted, there were varying results depending upon the particular metal which was to be removed.

EXAMPLE 7

A male beagle dog followed by inhalation of a mixture of isoflurane, nitrous oxide and oxygen. The oxygen supply was gradually reduced to approximately 60% $SpO_2$. The femoral artery and cephalic vein were cauterized to provide lines for arterial and venous blood sampling. The animal was administered intravenously sodium chloride with stabilized dissolved oxygen at a dose concentration of 33 ppm and dose volume of 500 ml. The results are given in Table 7 hereinbelow.

| Animal No. | Occasions | $SpO_2$ % | $pO_2$ mmHg | Sampling Site for $pO_2$ |
|---|---|---|---|---|
| 1001A | Pre-Dose | 49 | 26 | Venous |
|  | Pre-Dose | 49 | 25 | Arterial |
|  | Immediately Post-Dose End | 48 | 27 | Venous |
|  | Immediately Post-Dose End | 48 | 25 | Arterial |
|  | 10 min Post-Dose End | 49 | 25 | Venous |
|  | 10 min Post-Dose End | 49 | 26 | Arterial |
|  | 15 min Post-Dose End | 49 | 25 | Venous |
|  | 20 min Post-Dose End | 49 | 28 | Arterial |
|  | 30 min Post-Dose End | 55 | 27 | Venous |
|  | 35 min Post-Dose End | 56 | 29 | Arterial |
|  | 40 min Post-Dose End | 58 | 29 | Venous |
|  | 45 min Post-Dose End | 58 | 32 | Arterial |
|  | 50 min Post-Dose End | 60 | 32 | Venous |
|  | 55 min Post-Dose End | 61 | 32 | Arterial |
|  | 60 min Post-Dose End | 61 | 30 | Venous |
|  | 65 min Post-Dose End | 61 | 34 | Arterial |
|  | 70 min Post-Dose End | 62 | 34 | Venous |
|  | 75 min Post-Dose End | 64 | 39 | Arterial |
|  | 80 min Post-Dose End | 63 | ** | Venous |
|  | 85 min Post-Dose End | 62 | 34 | Arterial |
|  | 90 min Post-Dose End | 64 | ** | Venous |
|  | 95 min Post-Dose End | 62 | 39 | Arterial |
|  | 100 min Post-Dose End | 65 | 37 | Venous |
|  | 105 min Post-Dose End | 67 | 38 | Arterial |
|  | 110 min Post-Dose End | 67 | 37 | Venous |
|  | 115 min Post-Dose End | 66 | 37 | Arterial |
|  | 120 min Post-Dose End | 66 | — | Venous |
|  | 125 min Post-Dose End | 65 | 37 | Arterial |
|  | 130 min Post-Dose End | 64 | 35 | Venous |

-continued

| Animal No. | Occasions | SpO$_2$ % | pO$_2$ mmHg | Sampling Site for pO$_2$ |
|---|---|---|---|---|
| | 135 min Post-Dose End | 64 | 35 | Arterial |
| | 140 min Post-Dose End | 63 | 35 | Venous |
| | 145 min Post-Dose End | 64 | 37 | Arterial |
| | 150 min Post-Dose End | 65 | — | Venous |
| | 155 min Post-Dose End | 65 | 38 | Arterial |
| | 160 min Post-Dose End | 64 | 38 | Venous |
| | 170 min Post-Dose End | 68 | — | Venous |
| | 175 min Post-Dose End | 66 | — | Venous |
| | 185 min Post-Dose End | 67 | 40 | Arterial |
| | 190 min Post-Dose End | 65 | ** | Venous |
| | 195 min Post-Dose End | 65 | ** | Arterial |
| | 200 min Post-Dose End | 66 | 35 | Venous |
| | 205 min Post-Dose End | 65 | 39 | Arterial |

—: Unable to obtain value
**: Value outside readable range

EXAMPLE 8

A male beagle dog, prepared according to Example 6, was administered orally reverse osmosis water with stabilized dissolved oxygen at a dose concentration of 100 ppm and a dose volume of 250 ml. The results are given in Table 8 hereinbelow.

| Animal No. | Occasions | SpO$_2$ % | pO$_2$ mmHg | Sampling Site for pO$_2$ |
|---|---|---|---|---|
| 1002B | 15 min Pre-Dose | 60 | 29 | Venous |
| | Pre-Dose | 53 | 25 | Arterial |
| | 5 min Post-Dose End | 50 | 21 | Venous |
| | 10 min Post-Dose End | 53 | 16 | Arterial |
| | 15 min Post-Dose End | 59 | 19 | Venous |
| | 20 min Post-Dose End | 56 | 16 | Arterial |
| | 25 min Post-Dose End | 56 | 15 | Venous |
| | 30 min Post-Dose End | 97 | 223 | Arterial |

EXAMPLE 9

In this example, the male beagle dog was administered orally stabilized dissolved oxygen in a reverse osmosis water at a concentration of 100 ppm and a volume of 100 ml. The results are set forth in the Table 9 hereinbelow.

| Animal No. | Occasions | SpO$_2$ % | pO$_2$ mmHg | Sampling Site for pO$_2$ |
|---|---|---|---|---|
| 1003C | Pre-Dose | 58 | 29 | Arterial |
| | Pre-Dose | 60 | 30 | Venous |
| | 5 min Post-Dose End | 73 | 47 | Venous |
| | 10 min Post-Dose End | 75 | 51 | Arterial |
| | 15 min Post-Dose End | 79 | 47 | Venous |
| | 20 min Post-Dose End | 85 | 51 | Arterial |
| | 25 min Post-Dose End | 84 | 53 | Venous |
| | 30 min Post-Dose End | 82 | 56 | Arterial |
| | 35 min Post-Dose End | 81 | 52 | Venous |
| | 40 min Post-Dose End | 84 | 54 | Arterial |
| | 45 min Post-Dose End | 82 | 54 | Venous |
| | 50 min Post-Dose End | 87 | 57 | Arterial |
| | 55 min Post-Dose End | 84 | 52 | Venous |
| | 60 min Post-Dose End | 83 | 56 | Arterial |
| | 65 min Post-Dose End | 81 | 54 | Venous |
| | 70 min Post-Dose End | 84 | 58 | Arterial |
| | 75 min Post-Dose End | 79 | 52 | Venous |
| | 80 min Post-Dose End | 81 | 48 | Arterial |
| | 85 min Post-Dose End | 82 | 61 | Venous |
| | 90 min Post-Dose End | 86 | 57 | Arterial |
| | 95 min Post-Dose End | 90 | — | Venous |
| | 100 min Post-Dose End | 79 | 46 | Arterial |
| | 105 min Post-Dose End | 84 | — | Venous |
| | 110 min Post-Dose End | 80 | 52 | Arterial |
| | 115 min Post-Dose End | 77 | — | Venous |

—: Unable to obtain value

EXAMPLE 10

Human subjects were administered reverse osmosis water having a stabilized dissolved oxygen of 100 ppm. The blood oxygen level was then measured at varying time intervals. The results are set forth in FIGS. 4 to 10.

As will be noted, in all instances, the blood level oxygen increased and remained increased for varying periods of time.

I claim:

1. In a method for fixing a first fluid within a second fluid comprising the steps of mixing said first and second fluids together; the improvement comprising the steps of passing said fluid between two electrodes, a first one of said electrodes (105, 110, 115) being formed of a metallic material having a dielectric covering (106, 111, 116) thereon, a second one of said electrodes (107, 112, 117) being formed of a metallic material and being grounded; and applying a DC voltage (2) to said first one of said electrodes (105, 110, 115), said fluids being passed spirally through a treatment zone where said fluids are subjected to an electric field from said DC voltage.

2. The method of claim 1 wherein said voltage is more than +/−10 kV.

3. The method of claim 2 wherein said first fluid is a gas.

4. The method of claim 3 wherein said second fluid is a liquid.

5. The method of claim 4 wherein said first fluid is oxygen and said second fluid is water.

6. The method of claim 2 wherein said electric field has a voltage of at least ±15 kV.

7. The method of claim 2 wherein said first fluid is a gas and said second fluid is a gas.

8. The method of claim 2 wherein said fluid is for human consumption.

9. The method of claim 8 wherein said first fluid is oxygen and said second fluid is a fruit juice.

10. The method of claim 8 wherein said first fluid is oxygen and said second fluid is milk.

11. The method of claim 2 wherein said first fluid is oxygen and said second fluid is a flowable resin.

12. The method of claim 1 wherein said first fluid is a liquid and said second fluid is a liquid.

* * * * *